United States Patent [19]

Kuroda et al.

[11] Patent Number: 5,267,294
[45] Date of Patent: Nov. 30, 1993

[54] RADIOTHERAPY APPARATUS

[75] Inventors: Katsuhiro Kuroda, Hachiouji; Masatoshi Nishimura, Misato, both of Japan

[73] Assignee: Hitachi Medical Corporation, Tokyo, Japan

[21] Appl. No.: 872,046

[22] Filed: Apr. 22, 1992

[51] Int. Cl.⁵ .............................................. A61N 5/10
[52] U.S. Cl. ...................................... 378/65; 378/113; 378/137; 250/492.3
[58] Field of Search ............... 378/65, 64, 68, 10, 378/12, 13, 113, 121, 137, 138, 143; 250/492.1, 492.3, 493.1

[56] References Cited

U.S. PATENT DOCUMENTS

| | | | |
|---|---|---|---|
| 4,726,046 | 2/1988 | Nunan | 378/65 |
| 4,827,491 | 5/1989 | Barish | 378/65 |
| 5,117,829 | 6/1992 | Miller et al. | 378/65 |

FOREIGN PATENT DOCUMENTS 55-83900  6/1980  Japan.

Primary Examiner—David P. Porta
Attorney, Agent, or Firm—Antonelli, Terry, Stout & Kraus

[57] ABSTRACT

In order to construct a radiotherapy apparatus which can irradiate a point in the body of a patient in an optional direction with high accuracy, an accelerated electron beam is controlled electrically by using deflectors so as to irradiate a plurality of radioactive ray generating positions, a collimator is provided so that a radioactive ray generated from the positions can irradiate one point of a portion of the patient's body to be treated, and a gantry can be rotated mechanically.

15 Claims, 3 Drawing Sheets

RADIOTHERAPY APPARATUS

BACKGROUND OF THE INVENTION

1. Field of the Invention

This invention relates to a radiotherapy apparatus, more particularly to a radiotherapy apparatus having a radioactive ray generating mechanism using a high energy electron beam, and more particularly to a radiotherapy apparatus suitable for treating a point of a patient's body by applying radioactive rays to it in an optional direction.

2. Description of the Prior Art

A device to generate radioactive rays by using an electron beam that is accelerated to high energy by an accelerator so as to use the radioactive ray for treating has generally a construction as shown in FIG. 5. That is, an electron beam 2 is irradiated to a target 5 in a radiation head for generating radioactive rays so as to generate a radioactive ray 6 from the target 5. Such a radioactive ray generator is fixed on a radiating head 10 in general. Therefore, a change of a radiating direction or a radiated position of a radioactive ray is made by rotation of a gantry 11 and movement of a treating table 9. However, there is a problem of poor freedom of radiating directions, and as described in Japanese Patent Laid-Open Publication No. 55-83900, a radiating head can be turned around the gantry 11.

In order to radiate a radioactive ray to a point in the patient's body from optional directions, in the conventional radiotherapy apparatus it is necessary to operate the radiating head and the treating table in a complex way, and thus it is difficult to maintain the high accuracy which is required by actual medical treatment. Moreover, so as to apply a radioactive ray to a point of the patient's body from optional directions, an apparatus is known in which many radioactive ray generators using radioactive cobalt are fixedly arranged on a spherical surface, but there is a very troublesome problem in the keeping and handling of cobalt because of its radioactivity. It is desirable to radiate a radioactive ray generated by an electron beam to a point of the patient's body in an optional direction.

SUMMARY OF THE INVENTION

An object of the present invention is to provide a radioactive ray radiating apparatus using an electron beam in which a radioactive ray can be applied to a point with high positional accuracy in an optional direction.

In order to attain the above described object, a radiotherapy apparatus according to the invention comprises a deflector which deflects and controls electrically an electron beam accelerated by an accelerator so as to irradiate a plurality of radioactive ray generating positions, and a collimator to focus a beam of radioactive rays generated from a plurality of the above described radioactive ray generating positions to a very small point. When using an electron beam as the radioactive ray, the collimator is removed, and the deflector is constructed so as to focus the electron beam to the very small point.

As a preferred embodiment of the above described construction a plurality of radioactive ray generating positions are distributed in a curved line, for example, in an arc, on a two dimensional plane where a target including a heavy metal, for example, gold, is arranged to generate radioactive rays, and the gantry including a deflector and a target is rotated around a line which passes though the very small point.

In this invention, a position for generating a radioactive ray is distributed in a three dimensional way by using means for controlling electrically the radiating direction of radioactive rays which are irradiated on a very small point in an optional direction. That is, the radioactive ray can be generated from a plurality of points, instead of a single point as in the conventional apparatus. Moreover, a direction of the generated radioactive rays is controlled by using a collimator so as to irradiate a desired point in the patient's body. Therefore, if the electron beam is electrically controlled and is deflected to irradiate to the generating points of the radioactive rays, it can irradiate a very small point with a high accuracy, in an optional direction.

DESCRIPTION OF PREFERRED EMBODIMENTS

Figure 1A:
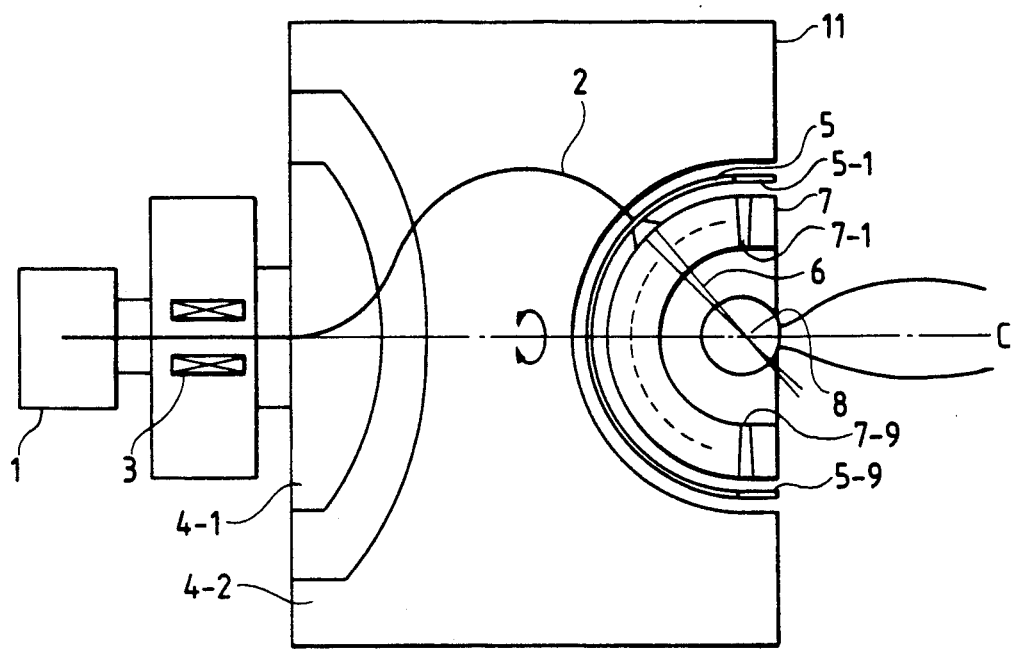
FIG. 1A and FIG. 1B are a plan view and a side view illustrating construction of an embodiment of a radiotherapy apparatus according to the present invention.

We will now describe embodiments of this invention referring to the drawings.

Figure 1B:
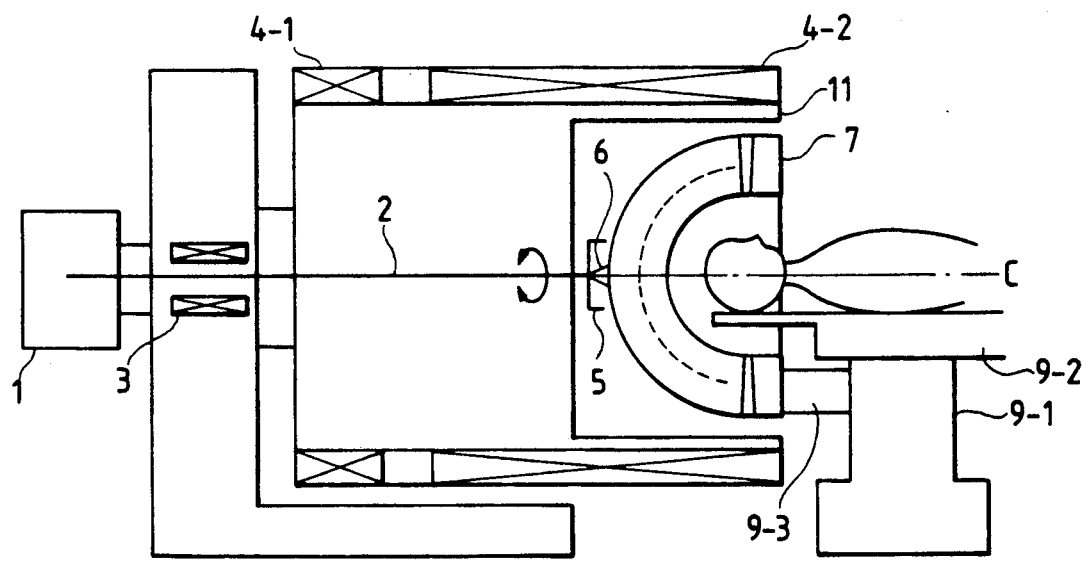

FIG. 1A and FIG. 1B are a plan view and a side view, respectively, of construction of an embodiment of a radiotherapy apparatus according to this invention.

An electron beam 2 accelerated by an accelerator 1 is focused by a quadrupole magnetic lens 3 to target 5. The focused electron beam 2 is deflected by deflectors 4-1 and 4-2, respectively, in opposite directions, and irradiates a circular arc target 5. The target 5 generates a radioactive ray 6 when the electron beam 2 irradiates it and the radioactive ray 6 is collimated by a collimator 7 and irradiates a very small point in the head of a patient at the center 8 of collimator 7. Scanning is performed by changing excitation of the deflectors 4-1 and 4-2. At that time, the electron beam 2 should always be focused sharply on the target 5. With this scanning, the radioactive ray 6 passed through the collimator 7 is focused on the very small point at the center 8.

Moreover, the deflectors 4-1, 4-2 and the target 5 are constructed as one unit (called a gantry 11) so as to be able to rotate around an axis C mechanically. Therefore, its rotation enables the radioactive ray 6 to irradiate the very small point 8 from different three-dimensional angles. In order to control an irradiating position of the radioactive ray with a high precision during the rotation of the gantry 11, too, the collimator 7 s fixed on a treating table 9-1 through a supporting rod 9-3. For this reason, the collimator 7 is formed as a hemispheric shell. The collimator 7 has a shielding function to prevent the radioactive ray 6 from irradiating a position other than the very small point at the center 8. Furthermore, a stage 9-2 is so constructed as to move upward and downward, left and right and in and out, and therefore a treating position is so adjusted as to come to just the center 8 of the collimator 7.

Figure 2:
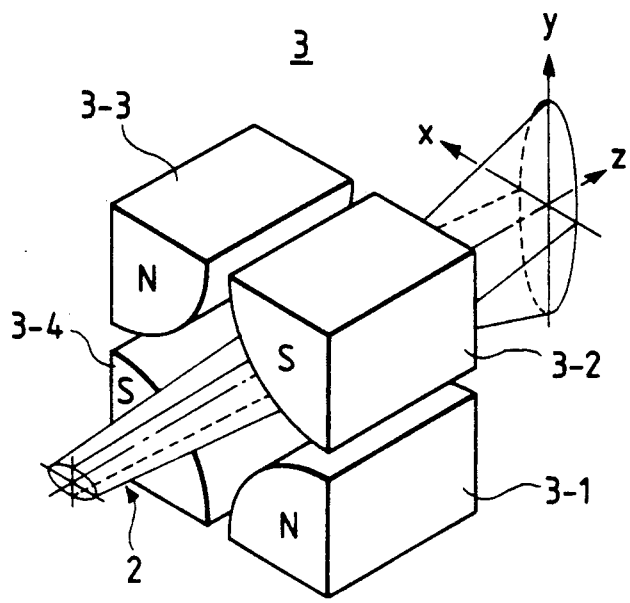
FIG. 2 is a schematic view illustrating construction of a quadrupole magnetic lens that is used for an embodiment of a radiotherapy apparatus according to the present invention.

FIG. 2 is a schematic view illustrating construction of the quadrupole magnetic lens 3 which is used for the above described embodiment. Four electromagnets 3-1, 3-2, 3-3 and 3-4 having respectively different polarities are arranged so that the electron beam 2 passes through their center. Actually, two or more sets of such four electromagnets are arranged in the direction of the electron beam 2.

In the next place, we will describe a more concrete construction of the above described embodiment.

A microtron is used for the accelerator 1, which generates the electron beam 2 of 6 Mev. The quadrupole magnetic lens 3 controls the electron beam 2 to form a beam having a diameter of about 5 mm on the target 5 even during scanning of the beam on the target 5 and the mechanical revolution of the gantry 11. By the way, deflectors of the magnetic field type are used for the deflectors 4-1 and 4-2 which deflect the electron beam 2, and gold is used for the target 5. The collimator 7 for collimating the radioactive rays 6 generated from the target 5 is formed semicircular lead of 10 mm in diameter on the target side 5 having a number of conical holes toward the center 8. For example, 24 pieces of lead are arranged approximately in a semicircle. An apparatus according to this embodiment is designed for therapy for diseases in a brain, for example, impaired functioning due to a cranical nerve disorder, cerbral tumor, a blood vessel deformity, etc.

Figure 3:
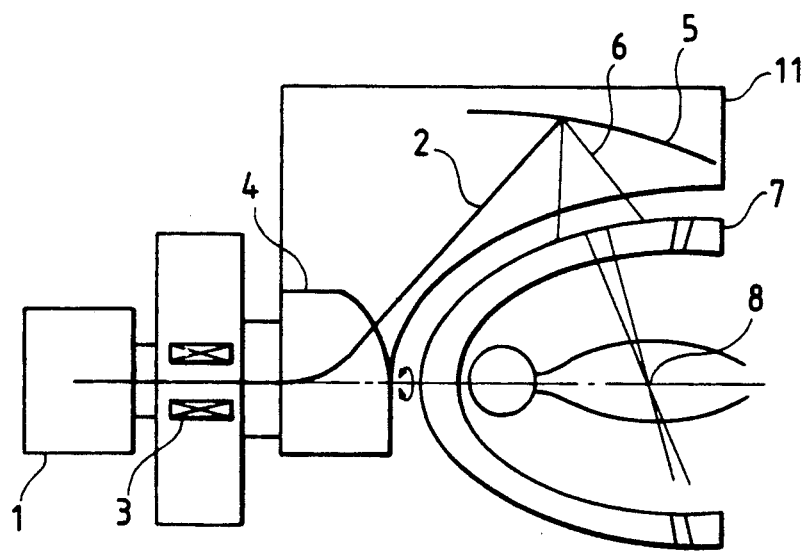
FIG. 3 is a side view illustrating construction of another embodiment of a radiotherapy apparatus according to the present invention.

FIG. 3 shows construction of another embodiment of the radiotherapy apparatus according to the present invention. This embodiment is suitable for radioactive ray therapy of the whole body, and its fundamental construction and principle of operation are the same as the embodiment of FIG. 1. But in the embodiment of FIG. 3, a radioactive ray 6 comes out from a target 5 in a radiating direction of an electron beam 2, and is used for therapy through a collimator 7. Moreover, although the electron beam 2 can be deflected in opposite directions, in the case of the radiotherapy apparatus according to FIG. 1, in this embodiment, deflection can be performed only in one direction in order to make dimensions of the apparatus small, and a gantry 11 is made to be able to rotate 360 degrees.

Figure 4:
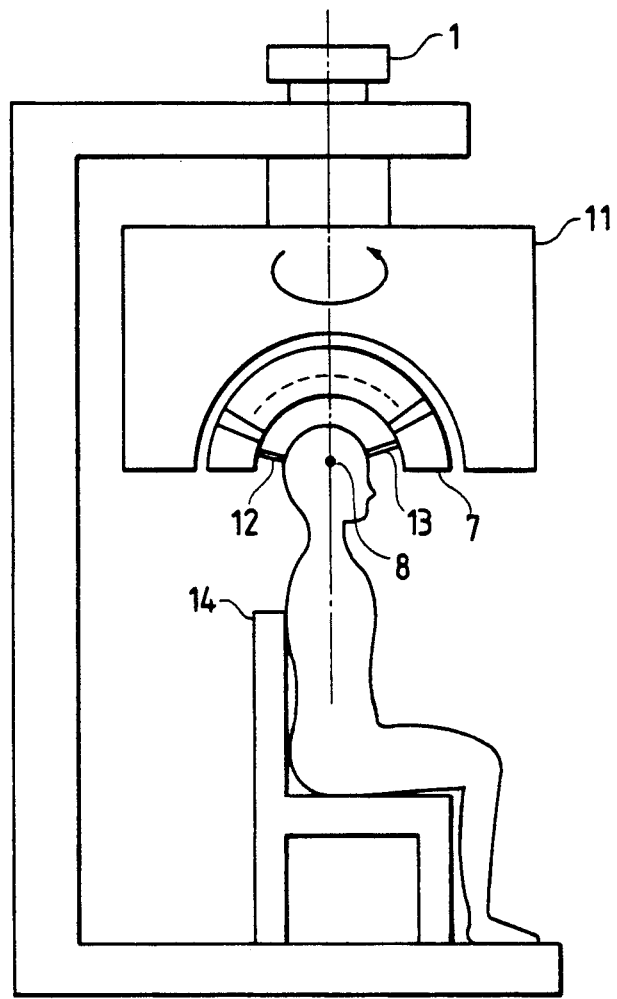
FIG. 4 is a side view illustrating construction of still another embodiment of a radiotherapy apparatus according to the present invention.
Figure 5:
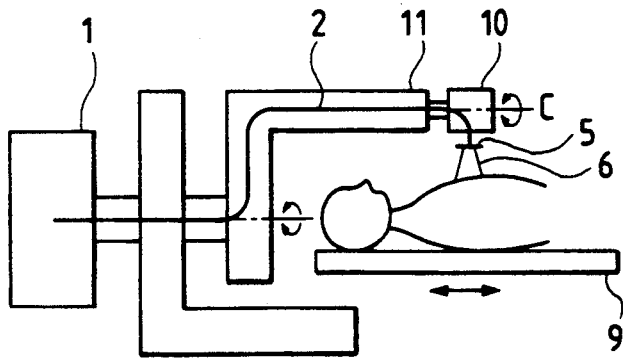
FIG. 5 shows schematically the construction of the conventional radiotherapy apparatus.

FIG. 4 shows still another embodiment of the radiotherapy apparatus according to the present invention. In this embodiment, a plurality of expandable and contractible support rods 12 and 13 are mounted on the collimator 7, and they are fixed on a body to be irradiated, for example, on the head of a patient. The support rods 12 and 13 are expanded and contracted to adjust the very small point to have the same position as the focusing point of the radioactive rays at the center 8 of the collimator 7.

So far embodiments of the present invention have been described but this invention is not limited to the above described embodiments. For example, inner diameters of the collimator may have a cylindrical or an inverted conical form so as to replace the collimator with one having dimensions suitable for the size of a body portion to be treated, such as the head, for example. Moreover the number of collimators, the beam dimensions on the target, the energy of electron beams, etc., are not limited to the above described examples. Also, types and forms of the target are not limited to that of the above described embodiments. For example, targets can be arranged discontinuously only at positions corresponding to holes of the collimators.

In the above described embodiments, the radioactive ray 6 is generated by irradiating the target 5 with the electron beam 2. However, the target 5 and the collimator 7 can be removed, and the electron beam 2 can be radiated directly to the treatment position as a radioactive ray. In this case, the electron beam is sharply focused at the central position 8 of radiation by using the lens 3. When using the electron beam directly for treatment, the energy of the electron beam should be changed depending on the depth of a treatment position because the electron beam has less penetrating capability than the radioactive ray. A microtron used for this embodiment can change the energy of the electron beam easily, so it can be changed dynamically depending on the radiating direction of the beam and the depth of the treatment position. Of course, the accelerator is not limited to that of the above described embodiment, and an accelerator such as a linac can be used.

After all, in the present invention, an electron beam is controlled and deflected electrically to irradiate a plurality of radioactive ray generating positions, a collimator is provided to make a radioactive ray generated from the positions irradiate a very small point, and the gantry can be rotated mechanically. In a radiotherapy apparatus according to the invention, an electron beam should be deflected electrically, so as to irradiate one point at the treatment position.

We claim:

1. A radiotherapy apparatus comprising:
   an accelerator for accelerating an electron beam;
   deflectors for deflecting the electron beam accelerated by said accelerator to irradiate a plurality of radioactive ray generating positions;
   radioactive ray generating means arranged corresponding to said plurality of radioactive ray generating positions, said radioactive ray generating means generating a radioactive ray when it is irradiated by said electron beam; and
   a collimator for collimating said radioactive ray so as to irradiate a point;
   wherein said radioactive ray generating means has a two dimensional arrangement, and said deflectors deflect and control the electron beam to irradiate a plurality of radioactive ray generating positions of said radioactive ray generating means in a vertical direction.

2. A radiotherapy apparatus according to claim 1, wherein said radioactive ray generating means is provided with a target, said target being made of gold.

3. A radiotherapy apparatus according to claim 1, wherein said collimator is of a fixed type, and said deflectors and said radioactive ray generating means are mechanically rotatable.

4. A radiotherapy apparatus according to claim 3, wherein said collimator has a curved surface for preventing said radioactive ray from irradiating other portions than said point.

5. A radiotherapy apparatus according to claim 1, further comprising quadrupole lenses for focusing the electron beam, wherein the deflectors are of a magnetic field type.

6. A radiotherapy apparatus according to claim 5, wherein an accelerating energy of the accelerator can be changed in accordance with a deflection provided by the deflectors.

7. A radiotherapy apparatus comprising:
an accelerator for accelerating an electron beam;
deflectors for deflecting the accelerated electron beam to irradiate a plurality of radioactive ray generating positions;
radioactive ray generating means disposed at least at the plurality of radioactive ray generating positions for generating a radioactive ray when the radioactive ray generating means is irradiated by the deflected electron beam at the plurality of radioactive ray generating positions;
a collimator having a surface with a plurality of apertures formed therein, the apertures being arranged in two dimensions on the surface of the collimator, each of the apertures collimating a radioactive ray generated by the radioactive ray generating means such that the collimated radioactive ray irradiates a point at which radiotherapy treatment is to be performed; and
a gantry having mounted thereon the deflectors and the radioactive ray generating means, the gantry being rotatable about an axis extending through the point at which radiotherapy treatment is to be performed.

8. A radiotherapy apparatus according to claim 7, wherein the radioactive ray generating means includes a gold target.

9. A radiotherapy apparatus according to claim 7, wherein the collimator is fixed relative to the point at which radiotherapy treatment is to be performed.

10. A radiotherapy apparatus according to claim 9, wherein the surface of the collimator is a curved surface, and the collimator prevents the collimated radioactive ray from irradiating points other than the point at which radiotherapy therapy is to be performed.

11. A radiotherapy apparatus according to claim 7, wherein the plurality of radioactive ray generating positions and the radioactive ray generating means are arranged in two dimensions in a plane, and the deflectors deflect the electron beam in the plane to irradiate the radioactive ray generating means at the radioactive ray generating positions.

12. A radiotherapy apparatus according to claim 11, wherein the radioactive ray generating means includes a gold target.

13. A radiotherapy apparatus comprising:
an accelerator for accelerating an electron beam;
a lens for focusing the accelerated electron beam at a point on an axis; and
deflectors for deflecting the focused electron beam to irradiate the point on the axis from arbitrary angles relative to the axis, the deflectors being rotatable about the axis such that the deflected electron beam can irradiate the point on the axis from arbitrary directions in a three-dimensional space.

14. A radiotherapy apparatus according to claim 13, wherein the lens is a quadrupole magnetic lens, and the deflectors are magnetic field type deflectors.

15. A radiotherapy apparatus according to claim 14, further comprising means for controlling the quadrupole magnetic lens to focus the accelerated electron beam at the point on the axis based on an angle of the electron beam relative to the axis and a rotation angle of the deflectors about the axis.

* * * * *